United States Patent [19]

Sayles

[11] 4,098,650
[45] Jul. 4, 1978

[54] METHOD AND ANALYZER FOR DETERMINING MOISTURE IN A MIXTURE OF GASES CONTAINING OXYGEN

[75] Inventor: Donald A. Sayles, Pittsburgh, Pa.
[73] Assignee: Thermo-Lab Instruments, Inc., Pittsburgh, Pa.
[21] Appl. No.: 739,713
[22] Filed: Nov. 8, 1976
[51] Int. Cl.² ............................................. G01N 27/46
[52] U.S. Cl. .................................. 204/1 T; 204/195 S
[58] Field of Search ............... 204/195 S, 195 W, 1 S, 204/1 W; 73/29, 23

[56] References Cited

U.S. PATENT DOCUMENTS

| Re. 29,209 | 5/1977 | Sayles | 204/1 T |
| 3,514,377 | 5/1970 | Spacil et al. | 204/1 T |
| 3,620,931 | 11/1971 | Reichner | 204/1 T |
| 3,851,520 | 12/1974 | Schluter et al. | 73/23 |

FOREIGN PATENT DOCUMENTS 2,404,006  8/1975  Fed. Rep. of Germany ........... 73/29

Primary Examiner—G. L. Kaplan
Attorney, Agent, or Firm—Stanley J. Price, Jr.; John M. Adams

[57] ABSTRACT

The moisture content of a gaseous mixture containing oxygen and the amount of other constituent gases in said mixture are determined by measuring, with an electrochemical cell, the ratio of oxygen partial pressures of a sample flow of said mixture and a comparison flow of a mixture of gases differing from said sample flow only by the reduction of the moisture content to a known level or, if moisture is not present, the reduction to a known level of the content of such other gaseous constituent. Also, provision is made to permit determining the amount of free oxygen in said gaseous mixture.

7 Claims, 2 Drawing Figures

METHOD AND ANALYZER FOR DETERMINING MOISTURE IN A MIXTURE OF GASES CONTAINING OXYGEN

BACKGROUND OF THE INVENTION

1. Field of the Invention

This invention relates to a method and apparatus for determining the condition of a gaseous mixture and, in particular for determining the moisture content, the molecular oxygen content and/or the content of other constituent gases in a gaseous mixture containing oxygen. Specifically, this invention relates to the use of a heated, ceramic, electrochemical cell for making these determinations.

2. Description of the Prior Art

Prior to this invention, a wide variety of devices and methods were employed for determining or measuring the amount of water vapor in a gaseous atmosphere. Some of the methods or devices used measured the equilibrium partial pressure of water in the gas. Others measured the temperature at which the condensation of water begins to occur upon cooling. Typical of the devices employed were those commonly identified as dew point hygrometers and absorption hygrometers. Characteristically, however, all such commonly employed devices were limited in their range of usefulness to relatively low concentrations of water, generally, under 20 percent by volume.

The use of a heated, ceramic, electrochemical cell is per se known in the art of gas analysis. Such cells are known to be useful to detect oxygen and/or combustibles in combustible mixtures and in the combustion by-products of a combustion process. Typical examples of these cells are disclosed in U.S. Pat. Nos. 3,597,345, 3,616,408, 3,865,707 and 3,869,370, the disclosures of which are incorporated herein by reference. However, as far as it is known, these cells have never been used to determine moisture content or the content of other gases in a gaseous mixture in accordance with the principles of this invention.

Accordingly, it has been found that a need exists for an improved method and apparatus for determining the moisture content of a gaseous mixture containing oxygen, as well as for determining the content of other gases in such a gaseous mixture. Moreover, it is found desirable, in conjunction with such an improved method and apparatus, to provide the capability of being able to determine the free or molecular oxygen content of said gaseous mixture. In particular, a need exists to be able to rapidly and reliably measure gaseous constituents in gas mixtures containing oxygen, to be able to measure the moisture content of such a gas to a much higher concentration than was heretofore readily accomplished and to be able to perform these determinations on such gaseous mixtures at highly elevated temperatures and/or on such gaseous mixtures containing corrosive gases, such as acid gases.

SUMMARY OF THE INVENTION

In accordance with the present invention, there is provided a method and apparatus for determining the moisture content of a gaseous mixture containing oxygen and the amount of other constituent gases in said mixture by measuring, with an electrochemical cell, the ratio of oxygen partial pressures of a sample flow of said mixture and a comparison flow of a mixture of gases differing from said sample flow only by the reduction of the moisture content to a known level or, if moisture is not present, the reduction to a known level of the content of such other gaseous constituent. More specifically, pursuant to this invention, there is provided both a means and method for determining the total amount of a constituent gas in a mixture of gases containing oxygen by providing a sample flow of said mixture of gases, contemporaneously providing a comparison flow of a mixture of gases differing from said sample flow only by the reduction to a known level of said constituent gas and measuring the ratio of oxygen partial pressures of said sample flow and said comparison flow. Also, provision is made to permit determining the amount of free or molecular oxygen in said gaseous mixture.

By following the teachings of this invention, it is now possible to measure higher proportions of water vapor in a gas mixture containing oxygen than was heretofore readily accomplished. As contrasted to known conventional devices, the useful range of measurement of the apparatus of this invention extends from about 2 percent water to about 98 percent water. Moreover, the apparatus of this invention can make such measurements, as well as measurements of the content of other gaseous constituents, in addition to free oxygen, at temperatures substantially higher than the operating temperatures of conventional devices and in gaseous mixtures containing a large amount of corrosive gases, such as sulfuric acid vapor, as is produced by the combustion of a fuel with a high sulfur content.

The foregoing and other objects, features and advantages of this invention will become more apparent when taken in conjunction with the following specification, the accompanying drawings and the appended claims.

DESCRIPTION OF PREFERRED EMBODIMENTS

Figure 1:
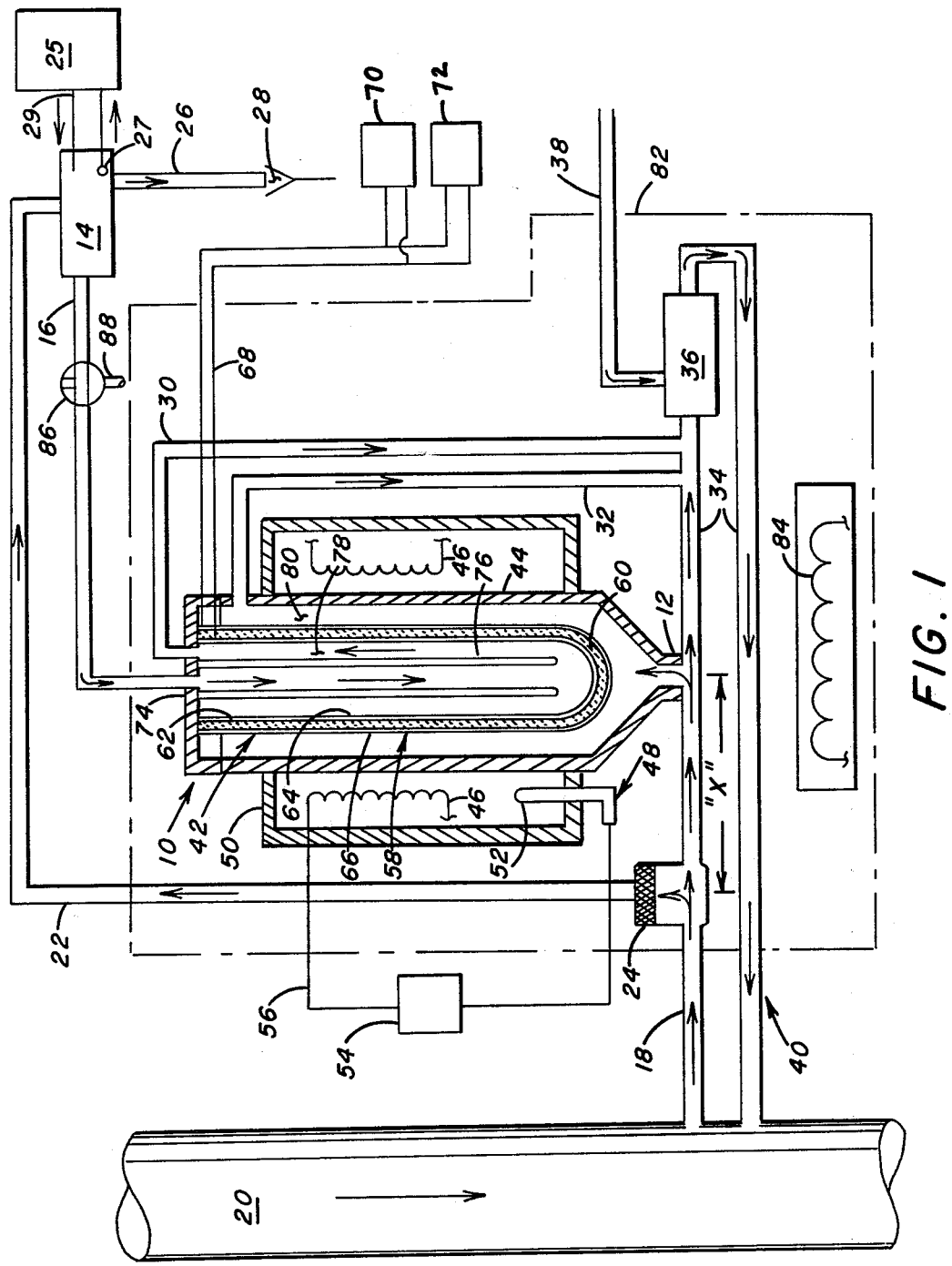
FIG. 1 is a schematic representation, partly in section, of a preferred arrangement of one embodiment of apparatus employed in the practice of this invention.

Referring to FIG. 1 there is shown schematically a typical apparatus arrangement of this invention for use in determining the moisture or water vapor content of a gas mixture containing oxygen, as well as optionally determining its free or molecular oxygen content. With reference to its use for gas moisture analysis, the apparatus basically comprises an electrochemical analyzer 10, a sample gas flow conduit 12 connected to the analyzer 10, a gas drier 14 and a comparison gas flow conduit 16 connected from the drier 14 to the analyzer 10.

Referring in greater detail to FIG. 1, a preferred plumbing or conduit arrangement, as shown, includes a sample gas header 18 connected to a chamber or main flow conduit 20 containing the gas mixture to be analyzed. Connected to header 18 is a drier inlet conduit 22, optionally containing in its flow path, from header 18 to drier 14, a particulate filter 24. Drier 14, as illustrated, is a cooler or condensor type drier which may be cooled by a thermoelectric "Peltier effect" device, by mechanical refrigeration, or by other means as desired. Accordingly, as will be understood by those skilled in the art, drier 14 includes a liquid seal (not shown) to allow condensate only to flow from the drier via drier liquid outlet 26 to condensate drain 28. Also provided are a condenser temperature controller 25 and a condenser temperature sensor 27, suitably connected by circuitry 29 to drier 14, to control the cooling and, thus, the drying in drier 14 to a predetermined level. Obviously, in lieu of a cooler or condenser type drier, alternate drying devices may be used, such as water permeable tubes, desiccants, or any combination of a cooling condenser with the foregoing.

As is further illustrated in FIG. 1, sample gas flow conduit 12 is connected to sample header 18 at a location downstream of the connection of drier inlet conduit 22 to sample header 18. It will be understood that the distance "X," between these respective connections, is preferably variable, so that the transport time or rate of flow for the wet and dried samples will be nearly equal, causing them to reach the sensing device or analyzer 10 with substantially the same time delay. Also shown connected to analyzer 10, as will become clearer hereinafter are a dried gas exhaust conduit 30 and a wet gas exhaust conduit 32, each of which are connected at their distal ends to sample gas exhaust conduit 34, which comprises a continuation of sample header 18 downstream of its connection to sample gas flow conduit 12.

Interposed in exhaust conduit 34, downstream of the connection of conduits 30 and 32 therewith, there is schematically shown an eductor device 36, which, as illustrated, may be an air operated aspirator provided with an aspirator air supply conduit 38. Obviously, other types of sample pumping devices other than air operated aspirators could be employed and separate devices may be used to move each stream. The exhaust gases from the outlet of eductor 36 could be released to the atmosphere but, for reasons that will be apparent from applicant's assignees copending application Ser. No. 739,712, filed Nov. 8, 1976, by David M. Capone and entitled "Method And Apparatus For Conveying A Gas Sample Through An Analyzer Chamber," the disclosure of which is incorporated herein by reference, it is preferred that the exhaust gases be returned via a loop conduit, as shown, to chamber or main flow conduit 20 at a location substantially parallel with and downstream of the connection of sample header 18 to chamber or conduit 20. In the context of said copending application, sample header 18, sample exhaust conduit 34 and eductor 36 may be collectively referred to as an eductive flow loop, generally designated by the numeral 40.

Reference is now made to the structure of electrochemical analyzer 10 which broadly includes an electrochemical cell 42 enclosed within an enlarged cell housing 44 and having a heater 46 disposed outside of the cell housing 44 to heat the cell 42 and housing 44. A temperature sensor 48 is also disposed outside of cell housing 44 and an insulating jacket 50 encloses heater 46 and the probe end portion 52 of sensor 48 with respect to cell housing 44. An external temperature controller 54 is connected by suitable circuitry 56 to heater 46 and sensor 48 to maintain the heat output of heater 46 at a preselected desired value so that cell 42 operates at a constant temperature. The preferred temperature to be produced within jacket 50 by heater 46 is in the range of 800° to 1800° F to achieve rapid response of the electrochemical cell 42, its accurate calibration and low resistance in the measuring circuit, to be described hereinafter. Insulating jacket or enclosure 50 confines the increased temperature primarily to cell housing 44 and electrochemical cell 42 and, accordingly, maintains a desired temperature differential between the sample gas flow conduit 12, shown interconnecting the lower portion of cell housing 44 with sample header 18, and wet gas exhaust conduit 32, to induce positive convective flow of the wet gas sample into conduit 12 and housing 44 and out through exhaust conduit 32.

The electrochemical cell 42, illustrated in the drawings, includes a ceramic oxide tube or tubular membrane 58, having a closed end portion 60 and an open end portion 62, which is composed of one of the ceramic oxides that exhibits electrolytic conductivity by means of oxygen ions, such as zirconium oxide containing an amount of calcium oxide, yttrium oxide or magnesium oxide and, also, thorium oxide containing yttrium oxide. The inside of ceramic oxide tube 58 is provided with a porous conductive coating or electrode 64, such as a porous platinum electrode coating, and the outside of the tube is provided with a similar porous conductive coating or electrode 66.

The coatings or electrodes 64 and 66 are connected through a circuit 68 to separate voltage measuring or readout devices 70 and 72 which, for reasons that will become apparent, are calibrated to respond to the EMF produced by the electrochemical cell to indicate the water content of the sample gas mixture on readout device 70 and the free oxygen content on readout device 72. Also, as shown schematically, the open end 62 of electrochemical cell tube 58 is closed with the fitting 74 supporting an elongated, open ended, dried gas inlet tube 76 that extends nearly to the closed end portion 60 of cell tube 58, along the central region of tube 58, to form an annular space 78 between the outside walls of inlet tube 76 and the coated inside walls of cell tube 58. As shown, comparison gas flow conduit 16 is connected through fitting 74 to the adjacent end of inlet tube 76 and dried gas exhaust conduit 30 is also connected through fitting 74 to the annular space 78. Further, fitting 74 provides a seal between electrochemical cell 42 and cell housing 44 and supports electrochemical cell 42 centrally of cell housing 44 so as to provide an annular space 80 therebetween. Wet gas exhaust conduit 32, as shown, is connected to this annular space 80 at the upper end portion of cell housing 44, adjacent fitting 74.

Also, as shown schematically in FIG. 1, the apparatus of this invention preferably includes an insulated enclosure or cabinet 82, shown in phantom, that houses analyzer 10 and as much of the conduit or piping connected thereto as is practical. Disposed within insulated cabinet 82 is a heater 84, the purpose of which, along with insulated cabinet 82, is to prevent possible condensation of moisture within analyzer 10 and any of the conduits conveying sample gas either to or from the analyzer 10.

The apparatus of this invention measures water vapor by comparing the concentration of oxygen in the original or wet gas sample with the concentration of oxygen in either a fully dried portion of the original or wet gas sample or a portion dried to a constant, known water content (or dew point). The fraction of water by volume in the original gas sample (W) is given by the formula:

$$W = 1 - \frac{(O_2)_W}{(O_2)_D}$$

where, $(O_2)_W$ = fraction of oxygen in the original wet sample and $(O_2)_D$ = fraction of oxygen in the dried sample.

The electrochemical cell 42 responds to the ratio of oxygen partial pressures (or oxygen concentrations) at its two electrodes 64 and 66 so that:

$$E = A T \log \frac{(O_2)_1}{(O_2)_2}$$

where,
(O$_2$)$_1$ and (O$_2$)$_2$ are the respective oxygen partial pressures in the gases in contact with electrodes 64 and 66,
T is absolute temperature,
A is a constant,
E is the EMF produced by the cell 42.

When the wet, original gas sample is circulated past one electrode of the electrochemical cell 42 and a fully dried sample past the other electrode, the resulting EMF indicates the amount of water in the original sample according to the formula:

$$W = 1 - \log^{-1} [E/AT]$$

However, it is not necessary that the dried portion of the sample be fully dried, only that it be dried to a known water content. When this is done the formula is:

$$W = 1 + W_D - \log^{-1} [E/AT]$$

where, $W_D$ is the fraction of water by volume in the partially dried sample.

The apparatus enclosed in cabinet 82 is ideally located directly against one wall of the chamber or conduit 20 containing the sample to be analyzed. Otherwise, the sample must be brought through a heated line or conduit to the sensor cabinet 82 to preclude condensation of moisture within said conduit. A portion of the wet sample is diverted from the sample header 18, in the direction of the arrows shown, brought to the drier 14 and then back into the heated cabinet 82 to the inlet of the fitting 74 sealed to the open end of electrochemical cell 42. The dried sample flows to the bottom of the inlet tube 76 and, then, upwardly out through the annular space 78, in contact with electrode 64, to either be vented to the atmosphere (not shown) or discharged through dried gas exhaust conduit 30, eductor 36 and sample exhaust conduit 34 to a downstream portion to chamber or conduit 20.

Contemporaneously, a portion of the wet sample flows upwardly, by convection, in the direction of the arrows shown, from sample header 18 into cell housing 44, through the annular space 80 in contact with electrode 66, to either be vented to the atmosphere (not shown) or discharged through wet gas exhaust conduit 32, eductor 36 and sample exhaust conduit 34 to chamber or conduit 20. Electrochemical cell 42 responds to the oxygen partial pressure difference between the dried or partly dried gas in contact with electrode 64 and the wet gas in contact with electrode 66 and produces an EMF that is a measure of the ratio of their oxygen partial pressures. Readout device 70 then transposes this EMF to indicate the total moisture content in the original or wet sample.

As another feature of this invention, a selector valve 86 can be optionally located, as shown, in the line from the drier 14 to the electrochemical cell 42 so that, in an alternate position of the selector valve 86, air or other gas of known oxygen partial pressure may be introduced by conduit 88 to the comparison or reference side of the electrochemical cell, instead of dried sample. In this mode of operation, in accordance with the teachings of U.S. Pat. No. 3,869,370, the electrochemical cell 42 will measure the molecular oxygen content of the wet gas sample or, more precisely, the ratio of its oxygen partial pressure to that of the air or other gas, and indicated on readout device 72 the total molecular oxygen content of the wet gas sample.

Figure 2:
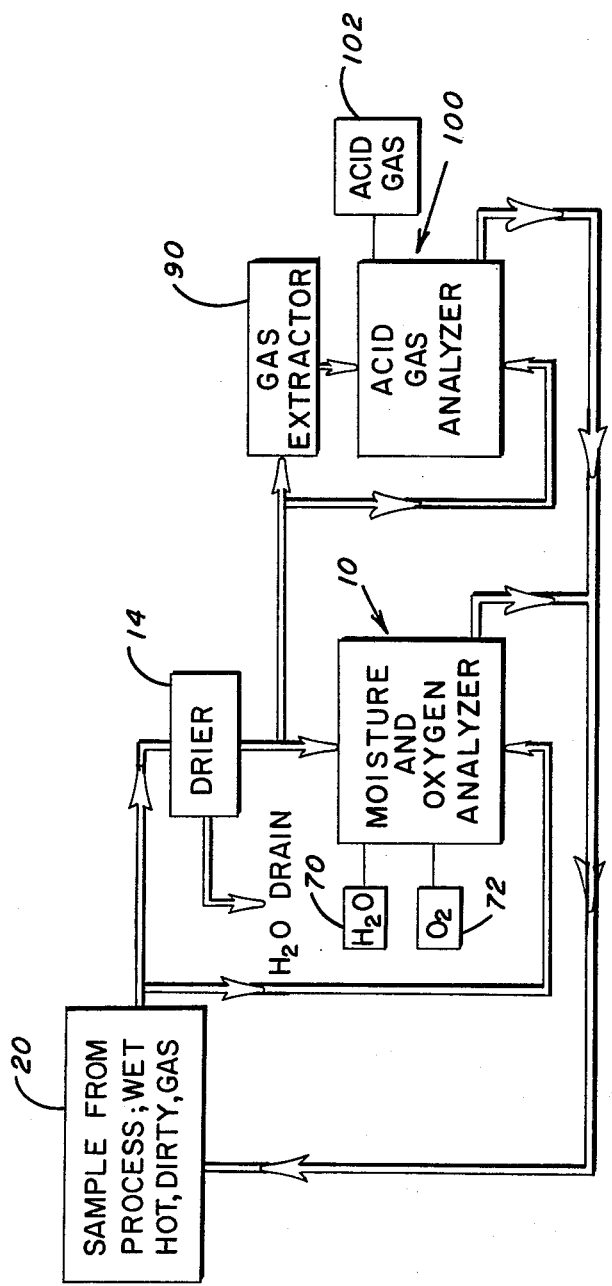
FIG. 2 is a block diagram of a preferred arrangement of another or expanded embodiment of apparatus employed in the practice of this invention.

With reference to FIG. 2, a further embodiment of this invention is shown in block diagrammatic form. In accordance with this embodiment, the content of one or more additional constituent gases, other than water vapor, can be determined. As shown, by removing a stream of dried gas from the arrangement shown in FIG. 1 or independently supplying a stream of dried gas and then splitting this stream with one portion going through a gas extractor 90 to reduce the concentration of the constituent gas to a known level and the other portion remaining unchanged, the respective portions are fed into an electrochemical cell analyzer 100 specific for oxygen in a similar manner as with the FIG. 1 embodiment. The electrochemical cell will then compare the oxygen partial pressures of the two portions and indicate, through appropriate circuitry alalogous to that described in connection with FIG. 1, the total content of the removed constituent gas in the original gaseous mixture on readout device 102. For example, after water has been removed, acid gases, such as sulfur trioxide, sulfur dioxide and carbon dioxide, can be individually and selectively removed in the gas extractor 90 by the proper choice of adsorbents or absorbents, such as molecular seive materials, silica gel or alumina, and the original or total concentration of each such removed constituent in the original gaseous mixture can be determined in the manner described. For convenience this latter electrochemical cell analyzer 100 is indicated in FIG. 2 as an "acid gas" analyzer, even though analysis may be made for other constituent gases therein.

According to the provisions of the patent statutes, I have explained the principle, preferred construction and mode of operation of my invention and have illustrated and described what I now consider to represent its best embodiments. However, it should be understood, that within the scope of the appended claims, the invention may be practiced otherwise than as specifically illustrated and described.

I claim:
1. A method for determining the total amount of water vapor in a mixture of gases containing oxygen which comprises,
   providing a first stream of said mixture of gases,
   providing a second stream of said mixture of gases,
   treating said second stream in a condenser to remove a portion of said water vapor and reduce the concentration of said water vapor in said second stream to a known level to form a treated second stream containing a known concentration of said water vapor,
   introducing said first stream and said treated second stream into a heated ceramic electrochemical cell, and
   measuring the ratio of oxygen partial pressures of said first stream and said treated second stream of gases.
2. A method as in claim 1 wherein the length of the streams are controlled so that the transport time for said first stream and said treated second stream will be nearly equal causing said streams to be measured with the same time delay.

3. A method as in claim 1 which includes cooling said condenser with a thermoelectric "Peltier effect" device.

4. A method as in claim 1 which includes cooling said condenser by mechanical refrigeration.

5. A method as in claim 1 which includes controlling the temperature of said condenser so that said second stream is dried to a known predetermined level.

6. Apparatus for determining the total amount of water vapor in a mixture of gases containing oxygen which comprises, means for providing a first stream of said mixture of gases, means for providing a second stream of said mixture of gases, means for treating said second stream in a condenser and removing a portion of said water vapor to provide a treated second gas stream containing a known level of said water vapor, means to introduce said first stream and said treated second stream into a heated ceramic electrochemical cell, and means for measuring the ratio of oxygen partial pressures of said first stream and said treated second stream of gases.

7. Apparatus as in claim 6 which includes means for intermittently replacing said treated second stream with a stream of air or other gas of known oxygen partial pressure.